United States Patent [19]

Stiefel et al.

[11] Patent Number: 4,551,480

[45] Date of Patent: Nov. 5, 1985

[54] COMPOSITIONS FOR THE TREATMENT OF PSORIASIS

[75] Inventors: Werner K. Stiefel, Coral Gables, Fla.; Daniel W. Nicolai, Delmar, N.Y.

[73] Assignee: Stiefel Laboratories, Inc., Coral Gables, Fla.

[21] Appl. No.: 585,515

[22] Filed: Mar. 2, 1984

Related U.S. Application Data

[63] Continuation-in-part of Ser. No. 506,414, Jun. 21, 1983, abandoned.

[51] Int. Cl.$^4$ .............................................. A61K 31/12
[52] U.S. Cl. .................................... 514/680; 514/863; 514/732
[58] Field of Search ........................................ 424/346

[56] References Cited

U.S. PATENT DOCUMENTS

| | | | |
|---|---|---|---|
| 3,029,188 | 4/1962 | Cyr et al. ................................ | 167/60 |
| 3,689,667 | 9/1972 | Lee ......................................... | 424/318 |
| 3,924,004 | 12/1975 | Chang et al. .......................... | 424/358 |
| 4,104,403 | 8/1978 | Barker et al. .......................... | 424/365 |
| 4,287,214 | 9/1981 | Van Scott et al. .................... | 424/346 |

OTHER PUBLICATIONS

Physicians' Desk Reference; 34th Edition, (1980), pp. 817, 1698–1699.
Journal of Pharmaceutical Sciences; vol. 70, No. 11, Nov. 1981, pp. 1205–1207.
Shroot et al., Brit. J. Derm., (1981), 105, Suppl. 20, 3.
Krebs et al., loc. cit., 6.
Cavey et al., loc. cit., 15.
Whitefield, loc. cit., 28.
Van Scott et al., loc. cit., 35.
Caron et al., loc. cit., 57.
Ingram, Brit. Med. Jorn., Sep. 12, 1953, 591.
Ponec-Waelsch et al., Arch. Derm. Forsch., 249,141, (1974).
Dictionnaire Vidal, 54th Ed., (1978), 1128–1129.
Kammerau et al., J. Inv. Dermatol., 1975, 64(3), 1459.

*Primary Examiner*—Leonard Schenkman
*Assistant Examiner*—Joseph A. Lipovsky
*Attorney, Agent, or Firm*—Bruce M. Collins

[57] ABSTRACT

A topical anthralin cream composition in which the anthralin demonstrates improved stability, comprises from about 0.05% to about 5% by weight of anthralin in a water: fluid hydrocarbon emulsion having a weight ratio of at least about 5:1, at least one anionic emulsifying agent, at least one oil soluble anti-oxidant, at least one water soluble acidic material, and at least one bifunctional sequestering agent.

16 Claims, No Drawings

COMPOSITIONS FOR THE TREATMENT OF PSORIASIS

CROSS REFERENCE

This is a continuation-in-part of Ser. No. 506,414, filed June 21, 1983, now abandoned.

DETAILED DESCRIPTION 1,8,9-Trihydroxyanthracene, also known as dithranol or anthralin, is one of the few effective agents available for the treatment of psoriasis. The compound, however, exhibits high irritancy to skin which is not afflicted with psoriasis, undesirable staining properties, and a tendency to be oxidized, leading to product instability. Historically, the compound has been formulated in heavy pastes and ointments such as Lassars paste and emulsifying ointments.

The utilization of oxalic acid to stabilize anthralin composition is described in U.S. Pat. No. 4,367,224. Such compositions are however anhydrous and take the form of a congealed yellow ointment.

The topical composition described in U.S. Pat. No. 4,203,969 represents a cosmetically more elegant anthralin formulation than prior formulations. Moreover, the spreadable composition described in that patent appears to satisfy some stability criteria in that excessive decomposition is not discernible upon U.V. analysis. More sophisticated analysis of this formulation, however, indicates that it is subject to undesirable transformations with the passage of time. In particular, high performance liquid chromatography (HPLC) has shown that although the overall pharmaceutical formulation appears to retain its stability, the anthralin dispersed in the oil phase undergoes unacceptable chemical change, not only reducing its effective concentration but also producing degradation products of unknown efficacy. While the structure of anthralin breakdown product(s) has not yet been fully elucidated, current evidence strongly suggests dimer formation; see e.g. Caron et al., Brit J. Derm., (1981) 105, Suppl. 20, 57.

The present invention pertains to improved aqueous anthralin formulations which are cosmetically acceptable and which exhibit significantly reduced chemical degradation of active ingredient, as compared with the prior art formulation.

The formulation described herein has certain features in common with the prior formulations of U.S. Pat. No. 4,203,969. In particular, it utilizes a two phase system of water and a hydrocarbon material. Moreover, the desirability of a water soluble acidic component such as citric acid or sodium bisulfite has been confirmed.

The present formulation, however, rather than utilizing a large proportion of hydrocarbon material as the anthralin-carrying phase, employs a predominantly aqueous vehicle, the ratio of water to hydrocarbon being at least on the order of 5:1. Secondly, the hydrocarbon, rather than being of the nature of the semi-solid petrolatum employed in the prior art, is largely fluid. Thirdly, the formulation includes at least one anionic emulsifier. Notwithstanding the high water content, the foregoing produces a high internal phase emulsion having an oil continuous phase and a water disperse phase. Fourthly, rather than utilizing a water-soluble, oil-insoluble antioxidant, the present composition employs precisely the opposite, namely an antioxidant which is oil soluble. Fifthly, the present composition includes a bifunctional sequestering agent.

In particular, the present invention pertains to an anthralin cream composition which comprises:

(a)
 (i) from about 0.05% to about 5% by weight of the composition, of anthralin in
 (ii) a water: fluid hydrocarbon emulsion wherein the weight ratio of water to fluid hydrocarbon is at least about 5:1 but which has an oil continuous phase;

(b) an emulsifying amount, up to about 3%, by weight of the composition, of at least one anionic emulsifier;

(c) from about 0.02% to about 2% by weight of the composition of at least one oil-soluble antioxidant;

(d) from about 0.5% to about 1%, by weight of the composition, of at least one acidic material; and (e) from about 0.02% to about 2% by weight of the composition of at least one bifunctional sequestering agent.

In addition to the foregoing components, the present composition advantageously can include one or more polyols such as glycerol, propylene glycol, sorbitol and the like, one or more hydroxybenzoic acid or alkyl ($C_1$–$C_4$) hydroxybenzoate preservatives such as salicylic acid, methylparaben, ethylparaben, and propyl paraben, and up to about 6% of an emulsifying agent which may be either, or preferably both, of a fatty alcohol and a non-ionic emulsifier.

The desirability of incorporating an antioxidant has been recognized in the prior art, but its role appears to have been directed towards curtailing oxidation of lipophobic components of the emulsifying agent. The requirement that the antioxidant be water soluble and oil-insoluble precluded that component from exerting its properties in the discontinuous hydrocarbon (oil) phase where the anthralin was primarily distributed. Although not wishing to be bound by any particular theory, it is believed that the large proportion of hydrocarbon material in the prior art composition reduced (but did not eliminate) decomposition by providing a high dilution factor for the anthralin. This, coupled with the semi-solid nature of the hydrocarbon, would result, by simple chemical kinetic principles, in a reduced incident of the reaction(s) involved in decomposition of active compound, whether the reaction was mediated by oxygen or otherwise. The relatively high content of hydrocarbon which consequently remained on the skin upon evaporation of the water phase, however, necessarily limited the effective concentration of active ingredient and moreover produced an oily, difficultly spreadable composition.

The present invention is based in part on the discovery that while the presence of an antioxidant is important to the stability of such anthralin emulsion formulations, it must be soluble in the hydrocarbon phase if the decomposition of the anthralin itself is to be inhibited. Unexpectedly, this discovery also has permitted a significant reduction in the proportion of hydrocarbon material (relative to the aqueous phase), as well as the use of more fluid hydrocarbon material.

Despite this significant reduction in the hydrocarbon content, the hydrocarbon component(s) constitutes the continuous phase of the emulsion. The hydrocarbon continuous phase is achieved by utilizing one or more anionic emulsifers, preferably fatty acid metal soap emulsifiers such as aluminum, calcium or magnesium stearate and/or a phosphonic ester salt of a mono- or diglyceride. The amount of emulsifier present will be at least that necessary to provide a stable emulsifying effect, which amount generally need be no more than about 3%, often less.

The use of such emulsifers in high internal phase water-in-oil emulsions in cosmetic formulations is described in U.S. Pat. No. 4,104,403. However, anionic emulsifiers prima facie would not appear to lend themselves to anthralin formulations since trace amounts of metals catalyse or initiate the decomposition of anthralin. However by incorporating an oil-soluble antioxidant in the formulation and by further providing at least one bifunctional sequestering agent, it is possible to formulate a high internal phase oil emulsion formulation of anthralin which not only demonstrates improved stability of both overall composition and active ingredient, but also has an esthetically pleasing cream-like cosmetic consistency permitting it to be easily spread and readily absorbed.

Suitable oil soluble antioxidants include such material as ascorbyl palmitate, alpha tocopherol, butylated hydroxytoluene, hydroxyquinone, and butylated hydroxyanisole. The amount included will depend upon the antioxidant potency of the material employed but generally a range from about 0.02 to about 2% by weight is satisfactory. It is not only possible but often desirable to employ several antioxidants in which case the content of each can be reduced. For example, satisfactory stabilization can be achieved by utilizing a three component oil soluble antioxidant mixture of approximately equal amounts of tocopherol, BHT and ascorbyl palmitate; e.g., 0.07% tocopherol, 0.05% BHT and 0.05% ascorbyl palmitate.

Desirably the formulation will contain other emulsifying agents such as higher alkanols; e.g., octyldecanol, particularly 2-octyldecanol and non-ionic surfactants such as polyglycerol oleate, glycerol oleate, propylene glycol cocoate, polyoxyethylene and 25 polyoxypropylene ethers and esters such as polyoxypropylene stearyl ether. The amount of such additional emulsifying agents which can be present will vary depending upon the effectiveness of the particular agent or combination. Significantly, however, because of the reduction of the hydrocarbon material which has been achieved and the use of the metal soap, the total amount of non-ionic emulsifers can be significantly reduced and seldom need exceed about 5% by weight. In fact in the preferred embodiment, the amount will be below 5%, e.g., from about 1 up to about 4.5%.

The hydrocarbon material typically will include one or more light mineral oils. Semi-solid hydrocarbons and paraffin can be dissolved therein but the proportion of these relative to the liquid hydrocarbon should not be so great that the overall hydrocarbon component loses its fluid nature. The hydrocarbon component acts as a solubilizer for the anthralin and its fluid nature permits the active ingredient to be easily spread and to penetrate the involved area. Typically, the total content of the fluid hydrocarbon in the composition, which includes normally solid hydrocarbon dissolved in normally liquid hydrocarbon, will be on the order of 10 to 15% by weight whereas the water content will be at least about 75% by weight and preferably about 80%. Hence a typical formulation could have 10.6% of a 2.3:3.3:6.0 mixture of petrolatum, paraffin and light mineral oil and 81% water, the ratio of water to hydrocarbon being about 7.6:1.

In addition to the foregoing components, there will be one or more water soluble components which satisfy at least one of the categories of an acidic material in an amount of from about 0.5% to about 1% by weight of the composition; and at least one bifunctional sequestering agent in an amount of from about 0.02% to about 2% by weight of the composition, both of said functional categories being satisfied.

Acidic materials are typically topically acceptable weak organic acids and weak inorganic acids and acid salts; e.g., malic acid, citric acid, salicylic acid, and sodium metabisulfite. Two or more such materials can be used in amounts of from 0.5% to 1% of the composition.

The bifunctional sequestering agent component includes such materials as disodium ethylenediamine tetraacetic acid and related chelating agents, thiourea, thioacetic acid, cysteine, tyrosine, nicotinic acid and sarcosine. Again, two or more such sequestering agents can be employed, the total content of which will range from about 0.02 to about 2% by weight.

Both functional categories must be satisfied but can be satisfied by the same compound. Thus some substances theoretically can fall within both categories of components and serve two functions. For example, malic, salicylic and citric acids, while acidic substances, can also serve as sequestering agents. (Salicylic acid also can functions as a hydroxylated benzoic acid derivative). The acidic material sodium metabisulfite, on the other hand, is not a sequestering agent so that a further component to satisfy this second functional category must be present. Several materials in each category can be present.

The composition is prepared by forming a hydrocarbon phase and an aqueous phase into which phases are added the various components. The selection of the phase to which a component is to be added is made on the basis of the component's preferential solubility; i.e., whether it is predominatly hydrophobic or hydrophilic. Heat can be utilized to facilitate production of homogenous individual phases and the homogenizing of the combined two phases to produce the emulsion. Any materials which are sensitive to excessive heat, such as tocopherol or tocopherol acetate, can be added subsequently.

Typical formulations utilizing the principles of this invention are as follows:

EXAMPLE 1

To 120 g of light mineral oil are added 46 g of 30 petrolatum and 46 g of paraffin. Fourteen grams of aluminum stearate are added to this hydrocarbon mixture as emulsifier, together with 30 g of polyglyceryl oleate and 60 g of 2-octyldodecanol. There then are added 4.8 g of anthralin and 0.4 g of ascorbyl palmitate as one oil soluble antioxidant. Finally 8 grams of salicylic acid are added and the whole is thoroughly blended at 90° C. This hydrocarbon phase will weigh approximately 330 g and will constitute approximately 16.5% of the final composition.

Separately, 1,646 g of deionized water are heated to approximately 90° C. and 18 g of citric acid are dissolved therein. To this is added 1.2 g of disodium ethylenediamine tetracetic acid and 5g of a 1.5:1 mixture of methylparaben and ethylparaben. When this aqueous mixture, which will weigh about 1,670 g and will constitute approximately 83.5% of the final composition, is homogenous, it is combined with the above hydrocarbon component in a homogenizer. When the emulsion is thoroughly blended, it is cooled to 50° C. and 0.6 g of tocopherol acetate are added. This mixture is further blended to produce 2,000 g of a 0.2% homogenous anthralin cream which maintains its formulation stability and in which the anthralin does not appear to undergo excessive degradation, e.g. less than 10% as determined by HPLC.

EXAMPLE 2

A 0.2% anthralin formulation is prepared according to the procedure of Example 1 utilizing the following components:

| Oil phase: | |
|---|---|
| mineral oil | 6.0% |
| paraffin | 2.3% |
| petrolatum | 2.3% |
| aluminum stearate | 0.7% |
| glyceryl oleate | 1.5% |
| anthralin | .22% |
| ascorbyl palmitate | .02% |
| octyldodecanol | 3.0% |
| salicylic acid | 0.4% |
| Water phase: | |
| deionized water | 68.82% |
| citric acid | 0.9% |
| Na$_2$EDTA | 0.06% |
| sorbitol (70%) | 13.5% |
| methyl paraben | 0.15% |
| propyl paraben | 0.10% |
| Alpha tocopherol | 0.03% |

EXAMPLE 3

A formulation is prepared following the procedure of Example 1, utilizing however 180 g of light mineral oil, 1556 g. of deionized water and 10 g. of Emulsynt 1055 (polyglycerol-4-oleate and polyethyleneglycol-8 propylene glycol cocoate).

EXAMPLE 4

A 0.4% anthralin formulation is prepared according to the proportions and procedure of Example 1, adding however a total of 1 g. of ascorbyl palmitate and 1.4 g. tocopherol together with 1 g. of butylated hydroxytoluene. The content of anthralin which is added is increased to 8.8 g. and the water to 1629 g. Finally, 2.09 g. of sodium bisulfite and 12 g. of disodium ethylenediamine tetraacetic acid are added to the water phase prior to emulsification.

EXAMPLE 5

Formulations of the following compositions are prepared in accordance with the procedure set forth in Example 1.

| Formulations: | % of Composition | | | |
|---|---|---|---|---|
| | 5A | 5B | 5C | 5D |
| Oil phase: | | | | |
| mineral oil | 6.0 | 6.0 | 6.0 | 6.0 |
| paraffin | 2.3 | 2.3 | 2.3 | 2.3 |
| petrolatum | 2.3 | 2.3 | 2.3 | 2.3 |
| aluminum stearate | 0.7 | 0.7 | 0.7 | 0.7 |
| glyceryl oleate | 1.5 | 1.5 | 1.5 | 1.5 |
| anthralin | 0.12 | 0.22 | 0.44 | 1.1 |
| ascorbyl palmitate | 0.05 | 0.05 | 0.05 | 0.05 |
| octyldodecanol | 3.0 | 3.0 | 3.0 | 3.0 |
| salicylic acid | 0.4 | 0.4 | 0.4 | 0.4 |
| butylated hydroxytoluene | 0.05 | 0.05 | 0.05 | 0.05 |

-continued

| Formulations: | % of Composition | | | |
|---|---|---|---|---|
| | 5A | 5B | 5C | 5D |
| Water phase: | | | | |
| deionized water | 81.66 | 81.56 | 81.34 | 80.68 |
| citric acid | 0.9 | 0.9 | 0.9 | 0.9 |
| Na$_2$EDTA | 0.60 | 0.60 | 0.60 | 0.60 |
| sodium bisulfite | 0.10 | 0.10 | 0.10 | 0.10 |
| Preservatives: | | | | |
| propyl paraben | 0.15 | 0.15 | 0.15 | 0.15 |
| methyl paraben | 0.10 | 0.10 | 0.10 | 0.10 |
| Tocopherol | 0.07 | 0.07 | 0.07 | 0.07 |

What is claimed is:

1. A topical anthralin cream composition in which the anthralin demonstrates improved stability, said composition comprising
   (a)
      (i) from about 0.05% to about 5%, by weight of the composition, of anthralin in
      (ii) a water:fluid hydrocarbon emulsion having an oil continuous phase wherein the weight ratio of water to fluid hydrocarbon is at least about 5:1;
   (b) an emulsifying amount up to about 3%, by weight of the composition, of at least one anionic emulsifying agent;
   (c) from about 0.02% to about 2% by weight of the composition, of at least one oil soluble antioxidant; and
   (d) one or more water soluble components which satisfy at least one of the functional categories of
      (i) an acidic material in an amount of from about 0.5% to about 1%, by weight of the composition; and
      (ii) at least one bifunctional sequestering agent in an amount of from about 0.02% to about 2%, by weight of the composition,
   both of said functional categories being satisfied.

2. A topical composition according to claim 1 wherein the oil soluble antioxidant component is one or more members selected from the group consisting of alpha tocopherol, alpha tocopherol acetate, ascorbyl palmitate, hydroquinone, butylated hydroxytoluene and butylated hydroxyanisole.

3. A topical composition according to claim 1 wherein the water soluble components include a sequestering agent which is one or more of disodium ethylenediamine tetraacetic acid, thiourea, thioacetic acid, cysteine, tyrosine, nicotinic acid and sarcosine.

4. A topical composition according to claim 1 wherein the water soluble components include an acidic material which is one or more of citric acid, malic acid, salicylic acid and sodium metabisulfite.

5. A topical composition according to claim 1 wherein the water soluble components include disodium ethylenediamine tetraacetic acid as the sequestering agent and citric acid, salicylic acid and sodium metabisulfite as the acidic material.

6. A topical composition according to claim 1 wherein the anionic emulsifying agent is a metal soap.

7. A topical composition according to claim 6 wherein the metal salt is aluminum stearate.

8. A topical composition according to claim 6 wherein one or more members selected from the group consisting of fatty alcohols, glycerol esters, polyoxyalkylene esters and polyoxyalkylene ethers are present as a nonionic emulsifying agent.

9. A topical composition according to claim 8 wherein the hydrocarbon is a mixture of light mineral oil, paraffin, and petrolatum and the nonionic emulsifying agent is a polyoxyalkylene ester.

10. A topical composition according to claim 1 wherein (i) the water:hydrocarbon ratio is at least 7:1 and the hydrocarbon is a mixture of light mineral oil, paraffin, and petrolatum; (ii) the oil soluble antioxidant component is one or more members selected from the group consisting of alpha tocopherol, alpha tocopherol acetate, ascorbyl palmitate, hydroquinone, butylated hydroxytoluene and butylated hydroxyanisole; (iii) the water soluble components include a sequestering agent which is one or more of disodium ethylenediamine tetraacetic acid, thiourea, thioacetic acid, cysteine, tyrosine, nicotinic acid and sarcosine, and an acidic material which is one or more of citric acid, salicylic acid and sodium metabisulfite; and (iv) the anionic emulsifying agent is a metal soap; the composition also including at least one nonionic emulsifying agent selected from the group consisting of fatty alcohols, glycerol fatty acid esters, polyoxyalkylene fatty acid esters and polyoxyalkylene fatty alcohol ethers.

11. A composition according to claim 1 comprising (i) from about 0.1 to about 1% anthralin in a water:hydrocarbon emulsion of about 6 to about 10% light mineral oil, from about 2% to about 3% petrolatum, from about 2% to about 3% paraffin and from about 75% to about 85% water; said composition also comprising (ii) an emulsifying amount up to about 1% of a fatty acid metal soap, (iii) a total from of about 0.1 to about 0.2% of one or more oil soluble antioxidants, (iv) from about 0.5 to about 1% of disodium ethylenediamine tetraacetic acid, (v) a total of from about 0.5 to about 1.5% of one, two, or three members selected from the group consisting of citric acid, salicylic acid, and sodium metabisulfite, (vi) from about 1 to about 5% of a higher alkanol and (vii) from about 1 to about 3% of a fatty acid monoester of glycerol or a polyglycerol.

12. A composition according to claim 1 comprising (i) from about 0.1 to about 1% anthralin in a water:hydrocarbon emulsion of about 6% light mineral oil, from about 2.2% to about 2.4% petrolatum, from about 2.2% to about 2.4% paraffin and about 80% water; (ii) about 0.7% of aluminum distearate, (iii) about 0.07% tocopherol, about 0.05% of butylated hydroxytoluene and about 0.05% ascorbyl palmitate as oil soluble antioxidants, (iv) about 0.6% of disodium ethylenediamine tetraacetic acid, (iv) about 0.9% of citric acid, (vi) about 0.4% salicylic acid, (vii) about 0.1% sodium metabisulfite, (viii) about 3% of octyldodecanol, and (ix) about 1.5% of polyglyceryl-4 oleate.

13. A composition according to claim 12 which contains about 0.1% anthralin.

14. A composition according to claim 12 which contains about 0.2% anthralin.

15. A composition according to claim 12 which contains about 0.4% anthralin.

16. A composition according to claim 12 which contains about 1% anthralin.

* * * * *